United States Patent [19]

Jones

[11] Patent Number: 5,217,592

[45] Date of Patent: Jun. 8, 1993

[54] ELECTROPHORESIS AND VACUUM MOLECULAR TRANSFER APPARATUS

[76] Inventor: Kenneth W. Jones, Department of Genetics, University of Edinburgh, The Kings Building, West Mains Road, Edinburgh, EH9 3JN, Scotland

[21] Appl. No.: 696,316

[22] Filed: Apr. 30, 1991

Related U.S. Application Data

[63] Continuation of Ser. No. 64,941, May 19, 1987, filed as PCT/GB86/00574, Sep. 26, 1986, abandoned.

[30] Foreign Application Priority Data

Sep. 26, 1985 [GB] United Kingdom ............... 8523801

[51] Int. Cl.⁵ .................... G01N 27/26; G01N 27/447
[52] U.S. Cl. ........................... 204/299 R; 204/182.8; 204/180.1
[58] Field of Search .............. 204/180.1, 299 R, 182.8

[56] References Cited

U.S. PATENT DOCUMENTS

| | | |
|---|---|---|
| 3,407,133 | 10/1968 | Olive et al. |
| 3,755,121 | 8/1973 | Schultz |
| 3,773,646 | 11/1973 | Mandle et al. |
| 4,151,065 | 4/1979 | Kaplan et al. |
| 4,181,594 | 1/1980 | Rizk et al. |
| 4,391,688 | 7/1983 | Hamelin |
| 4,415,418 | 11/1983 | Turre et al. |
| 4,452,901 | 6/1984 | Gordon et al. |
| 4,455,370 | 6/1984 | Bartelsman et al. |
| 4,589,965 | 5/1986 | Kreisher |

FOREIGN PATENT DOCUMENTS

| | | |
|---|---|---|
| 0161635 | 11/1985 | European Pat. Off. |
| 8702132 | 4/1987 | PCT Int'l Appl. |
| 2147609 | 5/1985 | United Kingdom |

OTHER PUBLICATIONS

Bethesda Research Laboratories, Inc., "Catalogue & Reference Guide", Aug. 1983, p. 51.
M. Peferoen et al. "Vacuum-blotting: a new simple and efficient transfer of proteins from sodium dodecyl sulfate-polyacrylamide gels to nitrocellulose" FEBS Letters vol. 145, No. 2 (Aug. 1982) pp. 369–372.
E. M. Southern, "Detection of Specific Sequences Among DNA Fragments Separated by Gel Electrophoresis", Journal of Molecular Biology, (1975), 98, 503–517.
M. Bittner et al., "Electrophoretic Transfer of Proteins and Nucleic Acids from Slab Gels to Diazobenzyloxymethyl Cellulose or Nitrocellulose Sheets", Analytical Biochemistry 102, 459–471 (1980).

Primary Examiner—John Niebling
Assistant Examiner—John S. Starsiak, Jr.
Attorney, Agent, or Firm—Bryan Cave

[57] ABSTRACT

An apparatus which includes the combination of a submarine gel tank, for the electrophoresic separation of, for example, nucleic acid molecules on agarose slab gels, with a vacuum applying means which transfers the separated molecules form the gel, without further handling, to a filter membrane by means of a controlled vacuum.

13 Claims, 2 Drawing Sheets

ELECTROPHORESIS AND VACUUM MOLECULAR TRANSFER APPARATUS

This is a continuation of U.S. application Ser. No. 07/064,941, May 19, 1987, filed as PCT/GB86/00574, Sep. 26, 1986, abandoned.

This invention relates to electrophoresis and vacuum transfer apparatus.

Separating macromolecules by electrophoresis on gel substrates is a well understood and common technique in the fields of chemistry, biology and medicine. There are basically two types of apparatus in common use. One incorporates a separating gel matrix between two glass plates placed vertically and in contact at both top and bottom with an electrophoresis buffer contained in reservoirs which are fitted with suitable electrodes, usually constructed of platinum wire. Samples are applied to the upper (cathode) surface of the gel and move down toward the lower (anode) under the influence of an applied voltage field. In the alternative system, a gel is cast in the horizontal position on a plate provided with raised edges which acts as the gel mould. Sample wells are cast into the gel by means of suitable slot-formers placed across the raised edges of the gel plate. The electrodes and buffer reservoirs are placed at either end of the gel and electrical continuity is achieved through the gel by, for example, suitable wicks or by immersing the gel completely in contact with the buffer reservoirs. In the latter mode the apparatus is usually referred to as a submarine gel tank.

On completion of electrophoretic separation of the macromolecules, gels are conventionally removed from the electrophoresis apparatus for further processing, in particular, for the recovery of molecules from the gel, or for photography or the like. In the case of deoxyribonucleic acid (DNA), if the purpose of separation is the specific identification of molecules by molecular hybridization, the gel is exposed to subsequent steps of processing. These are designed, for example, to reduce the molecular weight of large fragments by depurination in order to expedite their recovery, and/or to denature and equilibrate the duplex DNA in order to facilitate its adhesion to hybridization membranes, and to enable subsequent hybridization to take place. These steps conventionally require several separate gel-handling steps and typically may require 1-2 hours for completion.

The basic technique which is currently used to transfer molecules from suitably prepared gels onto filter membranes, for example nitrocellulose membrane filters, embodies the principles of diffusion and capillary flow and is referred to as "blotting". Typically, the gel is placed on filter paper in contact with a reservoir of transfer buffer, a suitable hybridization filter membrane is placed over the gel and is masked with plastic film to define the area from which molecules are to be transferred. A stack of dry absorbent paper towels is then placed over the mask and the filter membrane such that fluid flows from the gel and transfers molecules from the gel to the filter membrane. Blotting is of fundamental importance in the fields of molecular biology and biotechnology as an essential step in the analysis of macromolecules. Southern blotting refers to the transfer of molecules of deoxribonucleic acid (DNA); Northern blotting refers similarly to molecules of ribonucleic acid (RNA); Western blotting refers similarly to proteins.

Capillary flow and diffusion are inherently slow processes which, under conventional blotting conditions, tend to be bidirectional and are therefore a relatively inefficient means of transferring molecules from one planar substrate to another. The Southern blotting procedure also uses large amounts of refined paper products which are a continuing expense and are not readily available in some countries. An existing modification of the blotting technique avoids this and speeds up the process by using electrophoresis to accelerate transfer. In this case the method and its associated apparatus are commercially available and are commonly referred to as electroblotting. Electroblotting apparatus requires separate preparation and mounting of the gel after electrophoresis; processes which are time-consuming and inconvenient. The apparatus is relatively complex and expensive. In some cases artefactual bands may occur in the transferred pattern due to interference with voltage fields by structural components in the electrophoresis tank. Smaller molecules may be lost by passing through the filter membranes under the influence of the electrophoresis field.

Vacuum filtration of macromolecules from fluids is well known but has not been adopted for the recovery of macromolecules from gels, in the field of the present invention. However, the feasibility of so doing has been shown for proteins by M. Peferoen, R. Huybrechts and A. De Loof (FEBS Letters 145, number 2, pp369-372, 1982) and for DNA by Z. Zaitsev and A. G. Yakolev (Byulleten' Eksperimental'noi Biologii i Meditsiny of the USSR N. B. Bochkob Vol 96, Number 10, pp84-86 1983).

From the prior art processes as set out above, it will be appreciated that they have disadvantages in that they tend to be time consuming and involve an undesirable number of separate steps.

An object of the present invention is to obviate or mitigate the aforesaid disadvantages.

According to the present invention there is provided electrophoresis and vacuum transfer apparatus comprising a body for effecting separation of molecules by electrophoresis on a gel; filter means mounted in said body for receiving separated molecules thereon on transfer from the gel; and vacuum means connected to said body for applying a vacuum through said filter means to said body in order to induce transference of separated molecules from the gel to said filter means.

The apparatus which forms the subject of the present application has been found to be useful for the electrophotetic separation of macromolecules, particularly nucleic acids, in combination with the vacuum transfer of the electrophoretically separate molecules onto nylon-based filter membranes. The apparatus is designed so as to permit essential processing without handling the gel between electrophoresis and molecular transfer to hybridization membranes.

Preferably, the apparatus of the present invention includes a gel electrophoresis tank combined with a vacuum apparatus which is used to accelerate the movement of macromolecules from gels to suitable membrane filters after electrophoresis is complete. To effect this the apparatus preferably comprises an upper compartment in the form of a submarine gel tank incorporating suitable electrodes and provision for attaching sample well combs. This is placed over, and suitably secured to, a vacuum apparatus consisting of a vacuum chamber fitted with an adaptor for the attachment of a vacuum source. The upper side of this chamber, which acts as the lower part of the submarine gel tank, preferably consists of an inset porous support plate, composed, for example, of porous polyethylene, which permits the passage of fluids. The permeable area of this porous plate is controlled by an impervious demountable masking membrane. The opening in the masking membrane is slightly smaller than the nylon filter membrane to which molecules are to be transferred from the gel. This ensures that fluid transfer under vacuum is only possible via the gel. When the apparatus is assembled, the masking membrane is securely clamped between the vacuum chamber and the open upper section which constitutes the submarine gel tank. An O-ring set between the mating surfaces of the vacuum chamber and the submarine gel tank forms a fluid-tight seal. The filter membrane, which is nylon-based to avoid sticking to agarose gels when cast in situ, is suitably sealed in place so as to prevent molten agarose from contaminating the porous support plate and leaking into the vacuum chamber. The assembled apparatus is provided with a means of connected to a vacuum pump which is fitted with means of adjusting the vacuum strength within the narrowly defined limits which are essential for optimum transfer efficiency.

Embodiments of the present invention will now be described, by way of example, with reference to the accompanying drawings, in which.

Figure 1:
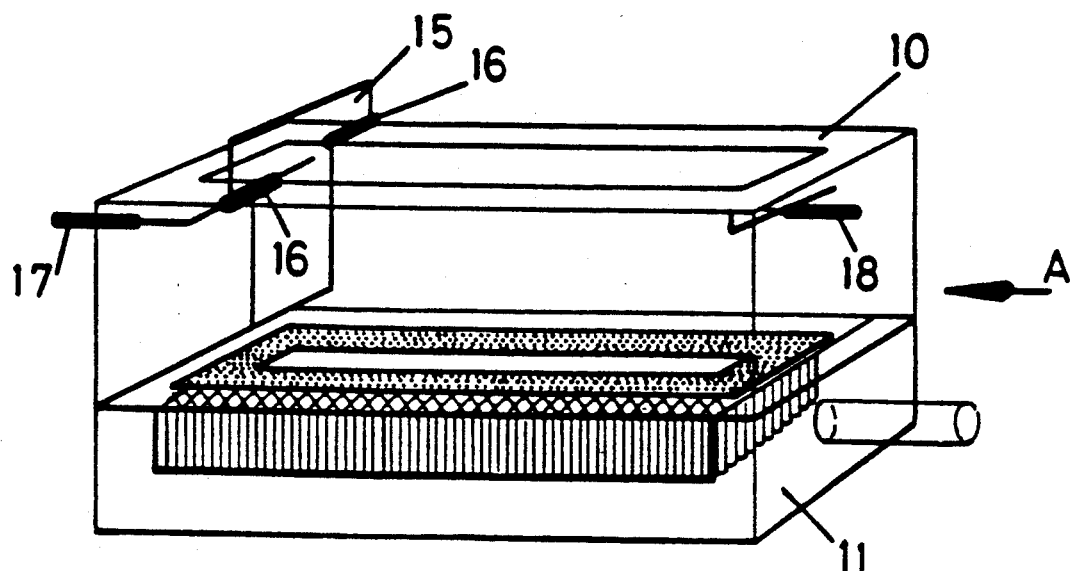
FIG. 1 is a perspective view of an assembled electrophoresis and vacuum molecular transfer apparatus in accordance with the present invention.
Figure 2:
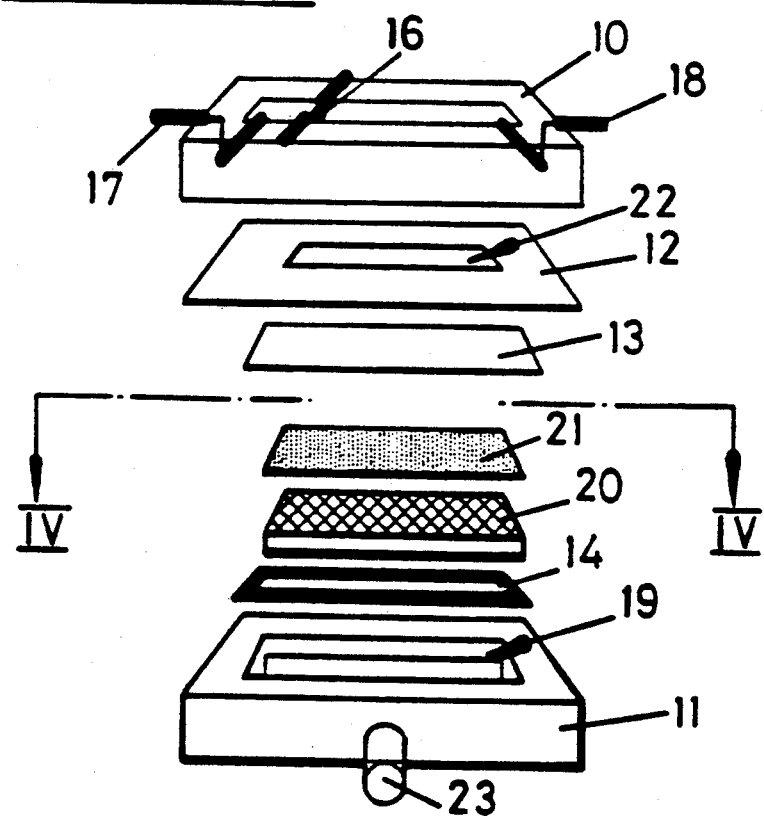
FIG. 2 is an exploded perspective view of the apparatus of FIG. 1 and viewed in the direction of arrow A in FIG. 1.
Figure 3:
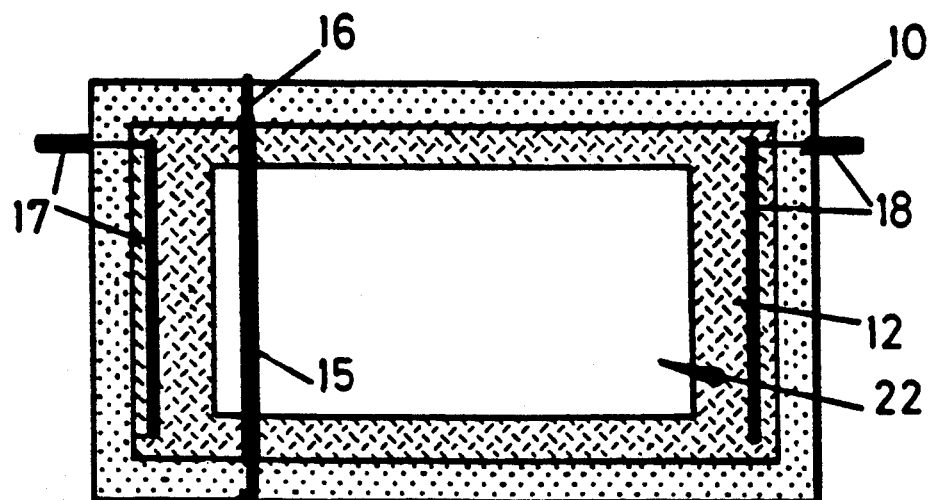
FIG. 3 is a plan view from above of the apparatus of FIGS. 1 and 2.
Figure 4:
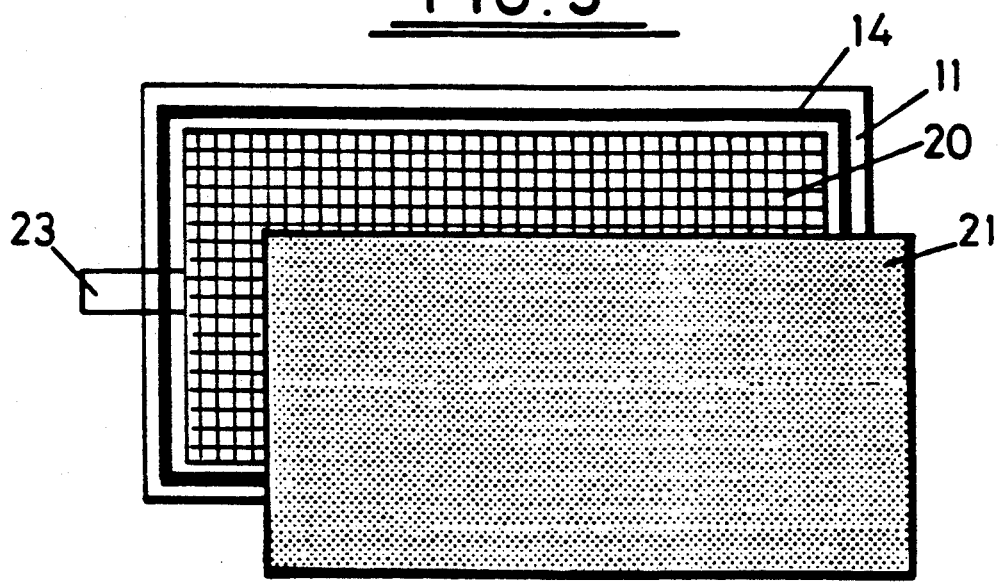
FIG. 4 is a perspective plan view on the line IV—IV of FIG. 2.

Referring to the drawings, an electrophoresis and vacuum transfer apparatus comprises an upper body portion of synthetic plastics material and which defines a submarine gel tank 10 and a lower body portion also of synthetic plastics material and which constitutes a vacuum chamber 11. The gel tank 10 is adapted to be superimposed on the vacuum chamber 11 and releasably secured thereto in order to sandwich therebetween a masking membrane 12 and a porous filter membrane 13 e.g. of nylon. A fluid tight seal is provided at the junction between the tank 10 and vacuum chamber 11 by an O-ring seal 14 located in the upper peripheral surface of the vacuum chamber 11 and which seals against the underside of the membrane 12.

The submarine gel tank 10 serves as a reservoir for subsequent preparation of a gel for molecular transfer and incorporates a sample well comb 15 located in slots 16 in the wall of the gel tank 10. The tank 10 is provided with a cathode 17 and an anode 18.

The vacuum chamber 11 has a rectangular internal recess 19 within which can be located a synthetic plastics spacer 20 of honeycomb structure and which supports a separate porous plate 21, e.g. of porous polyethylene, on its upper surface. When the spacer 20 and plate 21 are positioned in recess 19, the upper surface of plate 21 is substantially flush with the top edge of the vacuum chamber 11. The porous plate 21 permits the passage of fluid under vacuum and serves as a support for the filter membrane 13 and associated masking membrane 12 which masks the peripheral portion of the porous plate 21 to define a central area or field 22 thereof through which molecular transfer can take place from a gel to the filter membrane 13.

The vacuum chamber 11 is provided with a vacuum port 23 by means of which the vacuum chamber 11 can be connected in known manner to a vacuum pump (not shown).

Figure 5:
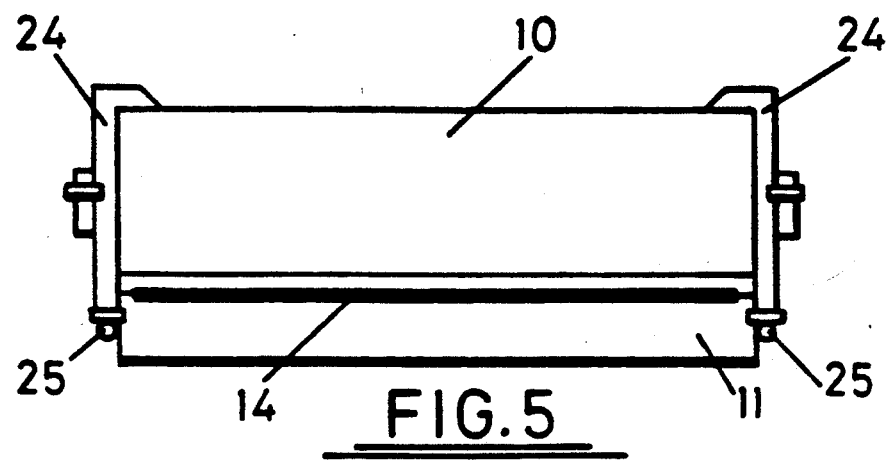
FIG. 5 is a side view of apparatus as shown in FIGS. 1 to 4 and incorporating one form of securing means for connecting the upper gel tank to its associated vacuum chamber.

As illustrated in FIG. 5, securing means are provided for releasably securing the upper gel tank 10 to the lower vacuum chamber 11. As shown in FIG. 5, the securing means comprises a pair of clips 24, each of which is fixedly hinged at 25 to the lower vacuum chamber 11 and which can be pivoted about its hinge 25 to engage the upper surface of the gel tank 10 in order to clamp it in operative relationship with the vacuum chamber 11. Although the securing means has been described in FIG. 5 as a pair of hinged clips 24, it will be readily appreciated the securing means can take other forms. For example, the secruing means can be constituted by elongated screws extending through the gel tank 10 to engage releasably the vacuum chamber 11.

If desired, a suitable trap can be provided to prevent liquids entering the vacuum pump.

In order to use the above-described electrophoresis and vacuum transfer apparatus, the spacer 20 is first placed within the recess 19 in the vacuum chamber 11. Alternatively, the spacer 20 can be reduced in depth and made integral with the body of the vacuum chamber 11. The porous plastics support plate 21 is then placed on the spacer 20 so as to form the upper surface of the vacuum chamber. The masking membrane 12, exceeding the area circumscribed by the O-ring seal 14 and with the unmasked area 22 slightly less than that of the gel area to be transferred is then placed over the support plate 21. The filter membrane 13 is sealed over the unmasked area 22 so as to provide a gel-tight seal during in situ gel casting. The upper submarine gel tank 10 is then placed over the masking membrane 12 and clamped in position on the vacuum chamber 11 by means of clips 24 so that the O-ring seal 22 engages the masking membrane 12 to make a fluid-tight seal around the periphery of the mutually engaging surfaces of the tank 10 and chamber 11. The sample well comb 15, which stops short of contacting the filter membrane 13, is put in place and its position is marked on the filter membrane 13 so as to note the original position of the applied samples. A gel slab is then cast in position on the filter membrane 13 to seal the entire space between the gel tank 10 and vacuum chamber 11. A suitable electrophoresis buffer is added to the gel tank 10 to cover the gel. Samples are added to the sample wells 15, suitable electrical connections are made to the electrodes 17,18 and electrophoresis is carried out in the usual manner. When the electrophoresis run is completed, the current is switched off, the electrophoresis buffer is aspirated out and successively replaced by the appropriate fluids to prepare the gel for molecular transfer. These preparatory fluids are finally replaced by transfer buffer, usually 20xSSC. The vacuum pump, connected via a fluid trap, is switched on and transfer of molecules from the gel to the filter membrane 13 is allowed to continue until complete, usually in approximately one hour.

The two separation functions of the apparatus can also be used independently of each other. Thus, the submarine gel electrophoresis module can be adapted for singular use by omitting the filter membrane 13 and inserting a suitable impermeable mask between the upper and lower modules i.e. the tank 10 and vacuum chamber 11. Likewise, the vacuum chamber module can be used separately to transfer nucleic acids from gels which have been processed in a separate electrophoresis tank. In this mode, the electrophoresed gel is placed over the masked aperture 22 so as to overlap its edges and in contact with the hybridization membrane 13 beneath. In this mode of use, since hot gels are not involved, transfers can be made to membranes other than nylon-based membranes. Alternatively, gels may be cast separately, before being placed in the apparatus for electrophoresis and transfer in the usual manner. In this case any type of hybridization membrane 13 may be employed. In this latter mode, the porous plate 21 and filter membrane 13 may be sealed off by a plastics sheet held in place under vacuum by switching on the vacuum pump. When electrophoresis is complete, the plastics sheet is removed allowing the electrophoresis buffer to drain away whilst the gel is positioned ready for vacuum transfer. Alternatively, in versions of the apparatus incorporating a shallow vacuum chamber, it is not necessary to seal off the submarine gel tank 10 from the vacuum chamber 11 as an insignificant volume of fluid would fill such a reduced space.

The pump used in connection with the blotting apparatus can be of any type providing that the vacuum level can be precisely controlled. An electrically driven diaphragm pump fitted with a vacuum gauge and regulator, for example an air bleed valve, to control the vacuum output is suitable. The vacuum is adjusted so that it will not collapse the gel, thereby restricting and reducing the molecular transfer, before the macromolecules of interest have moved out of it. A vacuum of not greater than 0.05 bar (50 cm.H$_2$O) is suitable for RNA and DNA transfer from agarose gels.

To disassemble the apparatus after transfer is complete the vacuum pump is switched off and the steps described above are carried out in the reverse sequence.

If desired, the apparatus can be constructed so as to be fully automatic in operation. In this mode, programmable pumps and fluid reservoirs are incorporated so as to permit all steps of fluid substitution to be carried out automatically.

For transfer of DNA by blotting in previously proposed methods, samples are first separated by electrophoresis on slab gels which are then transferred to a separate container and exposed first to a DNA denaturing solution and subsequently to a neutralising solution; a process which takes about 1-2 hours. The gel is then ready for blotting and is transferred to a suitable blotting apparatus. However, the apparatus of the present invention as described above has the inherent advantage that the gel slab to be blotted can be efficiently processed through blotting pre-treatments without being removed from the apparatus. Using this facility a DNA blot, for example, is denatured and neutralised in a few minutes.

From the above it will be seen that the present invention provides an apparatus which effectively combines the functions of separating macromolecules on gel substrates by electrophoresis and subsequently transferring them in situ to adsorbent substrates, without further handling, by by means of a controlled vacuum.

I claim:

1. In an apparatus for effecting electrophoretic separation of molecules in a gel,
   reservoir means for containing the gel in a body of liquid;
   support means in said reservoir for supporting said gel, said support means comprising a porous support member for supporting a filter medium on one side of which the gel is to be located;
   a pair of spaced electrodes within said reservoir means for applying an electric field across a predetermined portion of the gel; and
   vacuum means for applying a vacuum to the opposite side of said filter medium from said gel to transfer onto the filter medium the molecules separated in said gel in said reservoir means by said electric field.

2. The apparatus of claim 1 which includes securing means for releasably mounting said reservoir means on said vacuum means in a fluid-tight manner so as to clamp said support means therebetween.

3. The apparatus of claim 2 in which the securing means includes at least one clip for clamping said reservoir means and said vacuum means together.

4. The apparatus of claim 1 which includes means for providing at least one sample well in said gel.

5. The apparatus of claim 1 which includes an impervious masking membrane adjacent said support member for defining the area of application of the vacuum to the filter medium.

6. Transfer apparatus comprising:
   a tray having a bottom wall;
   platform means in said tray, said platform means including a porous support plate;
   said tray and platform means defining a chamber between said plate and said bottom wall;
   liquid reservoir means above said plate, said reservoir means comprising a wall extending above and surround the perimeter of said support plate and arranged to contain liquid above said support plate; and
   a fluid port communicating with said chamber for withdrawing fluid.

7. Apparatus for effecting electrophoresis and transfer of macromolecules to a filter, comprising:
   (a) a first chamber in which a gel is mounted;
   (b) electrodes within the first chamber for applying an electric field across at least a portion of the gel;
   (c) a second chamber disposed adjacent to the first chamber;
   (d) a partition separating the first chamber from the second chamber, and supporting the filter; and
   (e) means for effecting a pressure differential between the first chamber and the second chamber.

8. The apparatus of claim 7 wherein the macromolecules are nucleic acids.

9. The apparatus of claim 7 wherein the first chamber is a fluid containing reservoir.

10. The apparatus of claim 7, 8 or 9 wherein the filter means is selected from the group consisting of nylon membranes, hybridization membranes and filter membranes.

11. Apparatus for effecting transfer of macromolecules from a gel to a filter comprising:
   (a) a fluid containing reservoir;
   (b) a chamber disposed adjacent to the reservoir and a passage therebetween;
   (c) means for mounting the gel within the passage;
   (d) a permeable partition between the reservoir and the chamber which supports the filter;

(e) means for effecting a pressure differential between the reservoir and chamber; and (f) electrodes for applying an electric field across the gel.

12. Apparatus for effecting transfer of macromolecules from a gel to a filter comprising:

an open tank comprising a bottom and at least one upstanding wall; a liquid permeable partition dividing said open tank into a first compartment defined by said liquid permeable partition and said at least one upstanding wall and a second compartment defined by said liquid permeable partition, said bottom, and said at least one upstanding wall; said liquid permeable partition being capable of supporting said filter and said gel in said first compartment; and means for creating a negative pressure differential between the first compartment and said second compartment for transferring the macromolecules from said gel to said filter.

13. The apparatus of claims 12 wherein the filter means is selected from the group consisting of nylon membranes, hybridization membranes and filter membranes.

* * * * *